United States Patent [19]

Hildebrand

[11] Patent Number: 5,419,763
[45] Date of Patent: May 30, 1995

[54] PROSTATIC DRUG-DELIVERY CATHETER

[75] Inventor: Keith R. Hildebrand, Houlton, Wis.

[73] Assignee: CorTrak Medical, Inc., Roseville, Minn.

[21] Appl. No.: 177,332

[22] Filed: Jan. 4, 1994

[51] Int. Cl.6 .................... A61M 31/00; A61M 29/00
[52] U.S. Cl. ........................ 604/54; 604/101
[58] Field of Search ............. 604/20, 21, 53–55, 604/96–101; 606/192, 194

[56] References Cited

U.S. PATENT DOCUMENTS

| 2,854,982 | 10/1958 | Pagano | 604/101 |
|---|---|---|---|
| 4,423,725 | 1/1984 | Baran et al. | 604/101 |
| 4,573,966 | 3/1986 | Weikl et al. | |
| 4,610,662 | 9/1986 | Weikl et al. | |
| 4,655,746 | 4/1987 | Daniels et al. | 604/101 |
| 4,824,436 | 4/1989 | Wolinsky | 604/101 |
| 4,832,688 | 5/1989 | Sagae et al. | 604/101 |
| 4,909,785 | 3/1990 | Burton et al. | 604/54 |
| 5,007,897 | 4/1991 | Kalb et al. | |
| 5,114,423 | 5/1992 | Kaspryzyk et al. | 604/96 |
| 5,236,413 | 8/1993 | Feiring | 604/96 |
| 5,256,141 | 10/1993 | Gencheff et al. | 604/101 |
| 5,261,875 | 11/1993 | Spears | 604/101 |
| 5,312,343 | 5/1994 | Krog et al. | 604/101 |
| 5,315,992 | 5/1994 | Dalton | 604/101 |

Primary Examiner—C. Fred Rosenbaum
Assistant Examiner—Frank Wilkens, III
Attorney, Agent, or Firm—Merchant, Gould, Smith, Edell, Welter & Schmidt

[57] ABSTRACT

A method and apparatus for the treatment of a prostate gland which isolates the prostatic urethra from the membranous urethra and the bladder so that fluid may be transported into the prostatic ducts without compromising the openings to the prostatic ducts. One preferred embodiment incorporates balloons located at either end of the prostatic urethra to isolate the same.

9 Claims, 5 Drawing Sheets

PROSTATIC DRUG-DELIVERY CATHETER

TECHNICAL FIELD

The present invention relates to a catheter for the treatment of a prostate gland, and more specifically to a catheter that isolates the prostatic urethra from the membranous urethra and the bladder so that fluid may be transported into the prostatic ducts without compromising the openings to the prostatic ducts.

BACKGROUND

Many techniques exist for delivering drugs or other medicaments to body tissue. These techniques include oral administration; injection directly into body tissue, such as through an intramuscular injection; topical or transcutaneous administration where the drug is passively absorbed into, or caused to pass across, the skin or other surface tissue; and intravenous administration, which involves introducing a selected drug directly into the blood stream.

Except for topical or transcutaneous administration, the above drug delivery systems tend to be systemic. In other words, administration of the drug is delivered throughout the body by the blood stream. Transcutaneous drug delivery systems deliver a drug locally to a selected area, and are limited to external application of a drug through the patient's skin or other surface tissue. Thus, the above described drug delivery systems generally are not appropriate for the localized treatment of internal body tissue.

Although many medical situations are satisfactorily treated by the general systemic administration of a drug, there are many treatments that are facilitated and/or improved by the ability to deliver or administer a drug locally to a selected portion of internal body tissue, without appreciably affecting the surrounding tissue. One example is the prostate gland, which is subject to various diseases such as prostatitis, benign prostatic hyperplasia, and prostate cancer. The urethra allows relatively easy access to the prostate from outside the patient by means of a catheter.

The urethra includes the prostatic urethra and the membranous urethra. All of the major ducts of the prostate gland open on the surface of the prostatic urethra. These ducts extend into the prostate and branch into ductules (smaller ducts) and eventually end in acini (rounded sacs). The outside of the prostate gland is surrounded by a tough fibrous capsule that serves as a substantial physical barrier between the spongy prostatic tissue and the rest of the peritoneal environment. By using an appropriately designed catheter that is introduced through the urethra, it is possible to access the prostate via the prostatic ducts that extend deep into the gland.

Two previous patents have disclosed catheters for delivering drugs to tissue to the prostate gland via the prostatic urethra and the prostatic ducts. U.S. Pat. Nos. 5,007,897 and 4,423,725 disclose catheters having drug-delivery bladders made from a porous membrane. These patents teach placing the drug-delivery balloon into the prostatic urethra and inflating the balloon with a drug in a fluid form. The drug is pressurize,d so that it is caused to pass through the porous or perforated membrane and transported into the prostatic ducts.

There is a significant problem that results from delivering the drug through this type of membranous balloon. Specifically, the transport of the drug into the prostate gland is impeded and thus much less efficient.

There are two impediments. The first impediment is that the pressurized balloon expands and exerts a force against the walls of the prostatic urethra. This force compresses the prostatic tissue and causes the ducts to restrict and block the flow of the drug into the prostate gland. As a result, the drug typically does not distribute evenly throughout the ducts, nor throughout the prostate gland. Compression of the prostatic ducts also prevents or slows the flow of the drug solution into the interior of the prostate gland.

The second impediment is the porous membrane through which the drug solution must pass before it enters the prostatic ducts. Such an impediment slows the flow of the drug solution and results in additional inefficiency.

Slowing the flow of the drug solution results in longer delivery times and most likely lower levels of drug in the prostate gland. Additionally, a longer administration period requires additional time from the medical personnel. This expense is passed on to the patient, thereby increasing the cost of treatment.

Therefore, there is a need for a catheter that is capable of delivering drugs and diagnostic fluids to the prostate gland via the prostatic urethra and prostatic ducts, wherein the catheter does not compromise flow through the prostatic ducts by exerting pressure against the walls of the prostatic urethra.

SUMMARY

The present invention provides a catheter for treating the prostate gland which isolates the prostatic urethra from the membranous urethra and the bladder so that fluid may be transported into the prostatic ducts without compromising flow through the openings to the prostatic ducts and without substantial leakage of the fluid out of the prostatic urethra.

One preferred embodiment of the present invention comprises a catheter having two occlusion balloons separated by a distance that is approximately the same length as the prostatic urethra. Thus, no balloon exerts pressure against a significant portion of the prostatic urethra to cause a restriction of a significant portion of the prostatic ducts. The absence of a balloon in the prostatic urethra also means that there is no membrane interface between the drug and prostate gland to restrict the flow of the drug into the prostatic ducts.

The present invention delivers fluid to the prostatic urethra in the gap formed between the occlusion balloons. The fluid can then be pressurized so that it will transport through the prostatic ducts. Unlike current designs, the present invention allows for two independent inflation pressures. One pressure is for the occlusion balloons and the other pressure is for drug delivery. The ability to control the two pressures independently allows the operator to apply a higher pressure to the occlusion balloons than the pressure for the drug delivery. Thus, the operator can maximize the drug delivery pressure without having to be concerned that a significant amount of the drug can leak around the occlusion balloon and into the bladder or membranous urethra.

There is further advantage in the present invention in that a drug in a fluid form or a diagnostic fluid can be more evenly distributed throughout the prostate gland. Additionally, the drug or diagnostic fluid can be delivered quicker, thereby resulting in a shorter administrative time. The shorter administration time will also result in reduced medical expenses.

An additional advantage of the present invention is that the drug or diagnostic fluid is prevented from leaking into the membranous urethra or the bladder. The result is that a much higher percentage of the delivered fluid is transported into the prostate gland. Therefore, the fluid is conserved and waste is kept to a minimum.

One embodiment of the present invention comprises a catheter having distal and proximal ends, a drainage lumen, a plurality of inflation lumens, and a delivery lumen. A positioning balloon is operably connected to the distal end of the catheter and an inflation lumen is capable of passing fluid to the interior of the positioning balloon.

A proximal occlusion balloon is operably connected to the catheter and an inflation lumen is capable of passing fluid to the interior of the proximal occlusion balloon. A distal occlusion balloon is situated between the positioning balloon and the proximal occlusion balloon and operably connected to the catheter. A delivery lumen is capable of delivering a fluid to the interior of the distal occlusion balloon.

Additionally, the distal occlusion balloon is capable of isolating substantially all of the prostatic urethra from substantially all of the membranous urethra and the proximal occlusion balloon is capable of providing minimal leakage of fluid in the bladder. A delivery lumen is capable of passing fluid to the gap between the distal and proximal occlusion balloons. Pressurizing the fluid in the gap will cause it to be transported through the prostatic ducts.

In one preferred embodiment of the present invention, the proximal occlusion balloon and the distal occlusion balloon are separated by approximately 3 centimeters to approximately 6 centimeters.

The distance between the proximal and distal occlusion balloons is adjustable in an alternative preferred embodiment of the present invention. In the adjustable embodiment, the catheter comprises first and second parts wherein the distal occlusion balloon is operably connected to the first part and the proximal occlusion balloon is operably connected to the second part. The first part is slidably connected to the second part so that the distance between the distal and proximal occlusion balloons is adjustable.

One preferred embodiment of the present invention also comprises syringe-type pumps in fluid communication with the delivery lumens for injecting fluid into the gap between the proximal and distal occlusion balloons and pressurizing the fluid so that it is forced to transport into the prostatic ducts.

Still further embodiments comprise phonophoresis, iontophoresis, and/or electroporation capabilities to assist the transport of the drug into the prostatic ducts and into the prostatic tissue. A still further embodiment comprises a heating element positioned between the first and second occlusion balloons to heat the fluid and the prostatic tissue as it transports from the prostatic urethra into the prostatic ducts.

These and other advantages and features, which characterize the present invention, are pointed out with particularity in the claims annexed hereto and forming a further part hereto. For a better understanding of the invention, however, reference should be made to the drawings, which form a further part hereto and to the detailed description, which describes a preferred embodiment of the present invention.

DETAILED DESCRIPTION

One preferred embodiment of the invention will be described in detail with reference to the drawings, wherein like reference numerals represent like parts and assemblies throughout the several views. Reference to the preferred embodiment does not limit the scope of the invention, which is limited only by the scope of the claims attached hereto.

The present invention comprises a catheter with two balloons for isolating a target area for treatment. The catheter is capable of delivering fluid to the target area of the passageway that is isolated between the balloons. The present invention can be used to deliver fluid to the prostate gland and is advantageous in that the prostatic ducts remain substantially open, even when the balloons are inflated.

A catheter including two occlusion balloons is disclosed in commonly-assigned U.S. patent application Ser. Nos. 07/705,731, filed on May 24, 1991 and 07/937,464 filed on Aug. 28, 1992, both of which are incorporated by reference for the purpose of providing teachings regarding catheters that incorporate a plurality of occlusion balloons.

Figures 1, 2:
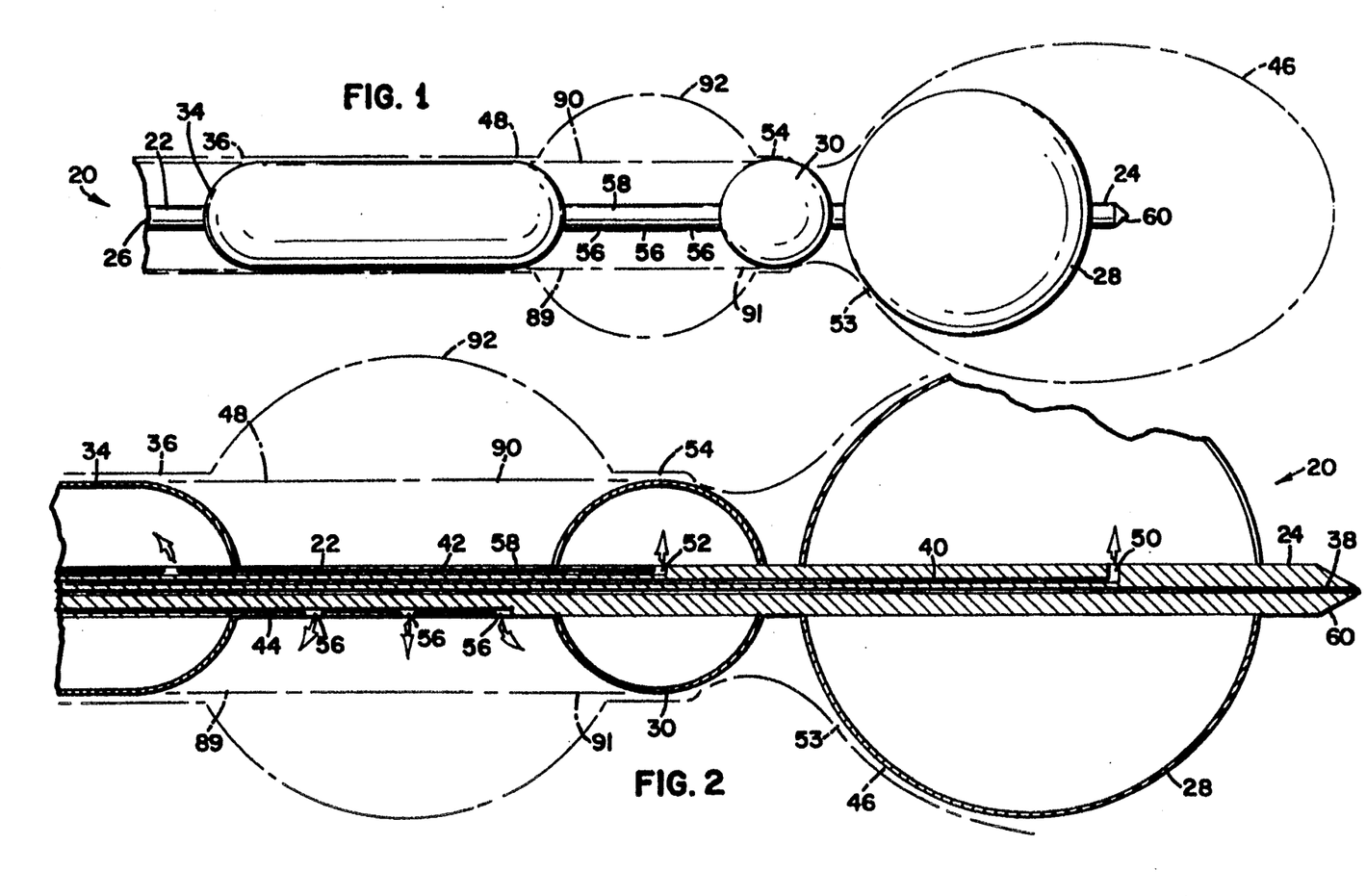
FIG. 1 is a view in partial cross-section of the catheter of the present invention located in the drug delivery position within the male urethra and bladder.
FIG. 2 is an enlarged cross-sectional view of the catheter of FIG. 1.

Referring now to FIGS. 1 and 2 which illustrate one preferred embodiment of a catheter according to the present invention, generally shown as 20, for isolating and treating a prostate gland. Catheter 20 has a catheter body 22 that includes a distal end 24 and a proximal end 26. Positioning balloon 28 is affixed to distal end 24 of catheter body 22 such that catheter body 22 passes through positioning balloon 28 and positioning balloon 28 is sealed to catheter body 22. Distal occlusion balloon 30 is affixed to catheter body 22 in a fashion similar to the method by which positioning balloon 28 is affixed. Distal occlusion balloon 30 is positioned on catheter body 22 such that distal occlusion balloon 30 will sit in the neck 54 of the bladder 46 when catheter 20 is located in its drug delivery position. Locating catheter 20 in the drug delivery position will be described in more detail below.

Proximal occlusion balloon 34 is affixed to catheter body 22 in a manner similar to distal occlusion balloon 30 and positioning balloon 28. The distance between distal occlusion balloon 30 and proximal occlusion balloon 34 is approximately the same length as the average prostatic urethra 90. Thus, distal occlusion balloon 30 and proximal occlusion balloon 34 isolate substantially all of the prostatic urethra 90 from substantially all of the membranous urethra 36 and substantially all of the bladder neck 54. Furthermore, proximal occlusion balloon 34 and distal occlusion balloon 30 are spaced far enough apart so that the balloons 30 or 34 exert minimal pressure against the wall of the prostatic urethra 90. Thus, a minimal number of prostatic ducts are caused to collapse when catheter 20 is in the drug delivery position, as described below. Preferably, the distance between distal occlusion balloon 30 and proximal occlusion balloon 34 is in the range from approximately 3 centimeters to approximately 6 centimeters. In order to accommodate prostatic urethras 90 of different lengths, medical personnel may have several catheters 20 available, each having different distances between the distal occlusion balloon 30 and proximal occlusion balloon 34.

Preferably, positioning balloon 28 has a diameter in the range of approximately 2 centimeters to approximately 4 centimeters when inflated. The most preferred diameter of positioning balloon 28 when inflated is 2.5 centimeters. Balloons 28, 30, and 34 can be made from either elastic material or inelastic material. Examples of suitable elastic materials include latex, polyurethane, or silicon. Examples of suitable inelastic materials include polyethylene, polycarbonate, or PET. However, the preferred material is polyurethane.

Catheter body 22 includes 4 lumens: drainage lumen 38, first inflation lumen 40, second inflation lumen 42, and delivery lumen 44. Drainage lumen 38 extends from distal tip 60 of catheter body 22 to proximal end 26. As described in more detail below, drainage lumen 38 drains urine from the bladder 46 when the catheter 20 is inserted into the urethra 48.

First inflation lumen 40 extends from the proximal end 26 to a position proximate the positioning balloon 28. First inflation port 50 passes from first inflation lumen 40 to the interior of positioning balloon 28 so that positioning balloon 28 can be inflated by injecting a fluid through first inflation lumen 40.

Second inflation lumen 42 extends from a position proximate proximal end 26 of catheter body 22, past proximal occlusion balloon 34, to a position proximate distal occlusion balloon 30. Second inflation port 52 passes from second inflation lumen 42 into the interior of distal occlusion balloon 30. Similarly, third inflation port 56 passes from second inflation lumen 42 to the interior of proximal occlusion balloon 34. Therefore, distal occlusion balloon 30 and proximal occlusion balloon 34 can be inflated simultaneously by injecting a fluid into second inflation lumen 42. One skilled in the art will appreciate that a third inflation lumen could be added to catheter body 22 so that distal occlusion balloon 30 and proximal occlusion balloon 34 could be independently inflated.

Delivery lumen 44 extends from a position proximate proximal end 26 of catheter body 22 to a position proximate the gap between distal occlusion balloon 30 and proximal occlusion balloon 34. Delivery ports 56 pass from delivery lumen 44 to the outer surface 58 of catheter body 22. Catheter body 22 may define as many as 20 delivery ports 56, which are macroscopic in size. Preferably, there are three or four delivery ports 56. The size of the delivery ports is preferably in the range from approximately 1 millimeter to approximately 2 millimeters. The most preferred size for the delivery ports is 1 millimeter.

The procedure for using catheter 20 is as follows. Catheter 20 is inserted into the urethra 48 using lubrication, sterile techniques, and any other technique that is commonly used to insert a Foley-type urological catheter. Catheter 20 is inserted into the urethra 48 until positioning balloon 28 enters the bladder 46 and is preferably inserted while there is urine within the bladder 46. Having urine within the bladder 46 is useful because the medical person who inserts catheter 20 will know that positioning balloon 28 has entered the bladder 46 when urine is observed in drainage lumen 38 or when urine can be aspirated through drainage lumen 38.

Once positioning balloon 28 is inserted within the bladder 46, fluid is injected through first inflation lumen 40 until positioning balloon 28 is inflated to a diameter of approximately 2 centimeters to approximately 4 centimeters. A predetermined, fixed volume of fluid is preferably used in order to prevent over inflation and bursting of positioning balloon 28. The fluid can be air, water, or saline, etc. However, the preferable fluid is sterile water.

After positioning balloon 28 is inflated, retrograde tension is applied to catheter 20 by pulling on the exposed portion of catheter body 22. This action seats positioning balloon 28 against the junction 53 between the bladder 46 and the neck 54 of the bladder 46. Retrograde tension is maintained by taping the exposed catheter body 22 to the patient's body. Catheter 20 is in the drug delivery position when positioning balloon 28 is seated against the junction 53 between the neck 54 and the, bladder 46.

When in the drug delivery position, distal occlusion balloon 30 is positioned so that it is primarily located in the bladder neck 54. However, a portion of distal occlusion balloon 30 may be located within the portion 91 of the prostatic urethra 90 closest to the neck of the bladder. The reason is that substantially all of the prostatic ducts open in the portion 89 of the prostatic urethra. Consequently, positioning distal occlusion balloon 30 in this manner causes a minimal amount, if any, of the prostatic ducts to seal shut when catheter 20 is in the drug delivery position. Additionally, proximal occlusion balloon 34 is located within the membranous urethra 36 and adjacent to, but not substantially within, the prostatic urethra 90.

After catheter 20 is located in the drug delivery position, distal occlusion balloon 30 and proximal occlusion balloon 34 are inflated by injecting a fluid into second inflation lumen 42. A predetermined, fixed volume of fluid is preferably used in order to prevent over inflation and bursting of distal and proximal occlusion balloons 30 and 34. The fluid can be air, water, or saline, etc. However, the preferred fluid is sterile water.

Drugs or diagnostic fluids may be delivered to the prostate gland 92 after catheter 20 is in the drug delivery position and positioning balloon 28, distal occlusion balloon 30, and proximal occlusion balloon 34 are inflated. One skilled in the art will realize that a pressure gauge and syringe can be placed in fluid communication with delivery lumen 44 to deliver the drug or diagnostic fluid to the prostatic urethra 90. Any number of types of syringes may be used such as a standard syringe, an adjustable syringe, or a syringe pump. However, an adjustable syringe is preferably used. An adjustable syringe is one that has threads or some other type of self-locking mechanism.

Once delivered, the drug or diagnostic fluid is pressurized, thereby transporting it into the ducts, ductules, and acini. The pressure on the fluid may range between from approximately 0.1 psi to approximately 10 psi. However, the preferable pressure is between approximately 1 psi and approximately 6 psi. The most preferred range of pressure is between approximately 2 psi and approximately 5 psi. This pressure causes the fluid to fill the prostatic ducts, ductules, and acini.

Preferably, a constant pressure should be maintained over a period of time ranging from approximately 0.25 hours to approximately 4 hours. The preferred range of time is between approximately 0.25 hours to approximately 2 hours, and the most preferred range is between approximately 0.25 hours and approximately 0.5 hours. One skilled in the art will realize that the precise amount of time will vary depending on the drug or the diagnostic agent being employed.

Maintaining constant pressure over a period of time, rather than a simple administration of a fixed volume of drug solution, will more likely result in homogeneous prostatic tissue concentrations. If accurate drug dosing is not required, a fixed volume of solution can be simply administrated. An example of when a fixed volume of solution is appropriate is when a positive contrast agent is introduced into the prostate gland 92.

The preferable procedure for withdrawing catheter 20 from the urethra 48 depends on whether toxic or caustic agents were delivered. For nontoxic drugs and diagnostic fluids such as antibiotics, anti-inflammatories, positive contrast agents, etc., the pressure of the fluid is simply reduced to zero, positioning and occlusion balloons 28, 30, and 34 are deflated, and catheter 20 is removed from the urethra 48.

If toxic or caustic agents were delivered, an alternative procedure for withdrawing catheter 20 is preferred. More specifically, a slight negative pressure is applied to the fluid in order to remove the excess drug or diagnostic agent from the prostatic urethra 90 after the administration period is complete. The prostatic urethra 90 may then be flushed with a saline solution. The saline solution is added and removed via delivery lumen 44 in the same fashion the drug or diagnostic fluid was initially delivered to the prostatic urethra 90. After the saline solution is removed, positioning and occlusion balloons 28, 30, and 34 are deflated and catheter 20 is removed.

Figure 3:
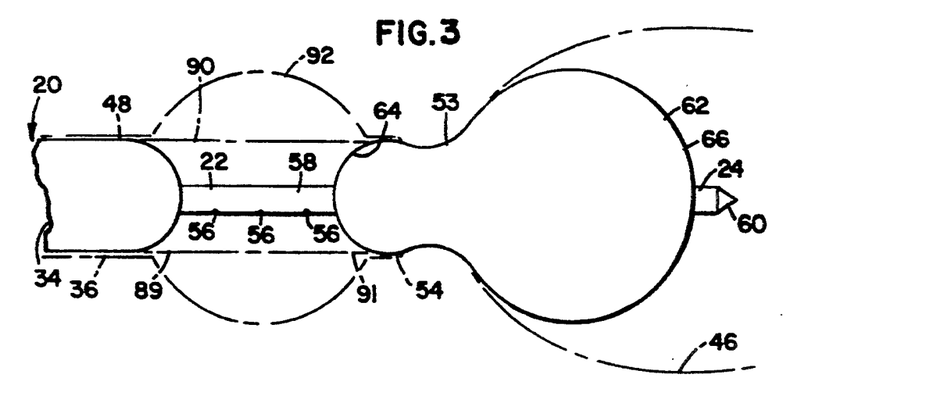
FIG. 3 is a partial view in partial cross-section of an alternative embodiment of a catheter according to the present invention, in which the positioning balloon and the distal occlusion balloon are combined into a unitary balloon.

FIG. 3 illustrates a first alternative embodiment in which a pear-shaped balloon 62 serves as a unitary positioning balloon and distal occlusion balloon. More specifically, pear-shaped balloon 62 has a narrow portion 64 for isolating the prostatic urethra 90 and a wide portion 66 for locating catheter 20 in the drug delivery position. One skilled in the art will realize that catheter body 22 may have either a common inflation lumen for both proximal occlusion balloon 34 and pear-shaped balloon 62, or have separate delivery lumens for these balloons 34 and 62. One skilled in the art will further realize that this alternative embodiment is used in a fashion similar to the embodiment described above.

Figures 4, 4A, 4B:
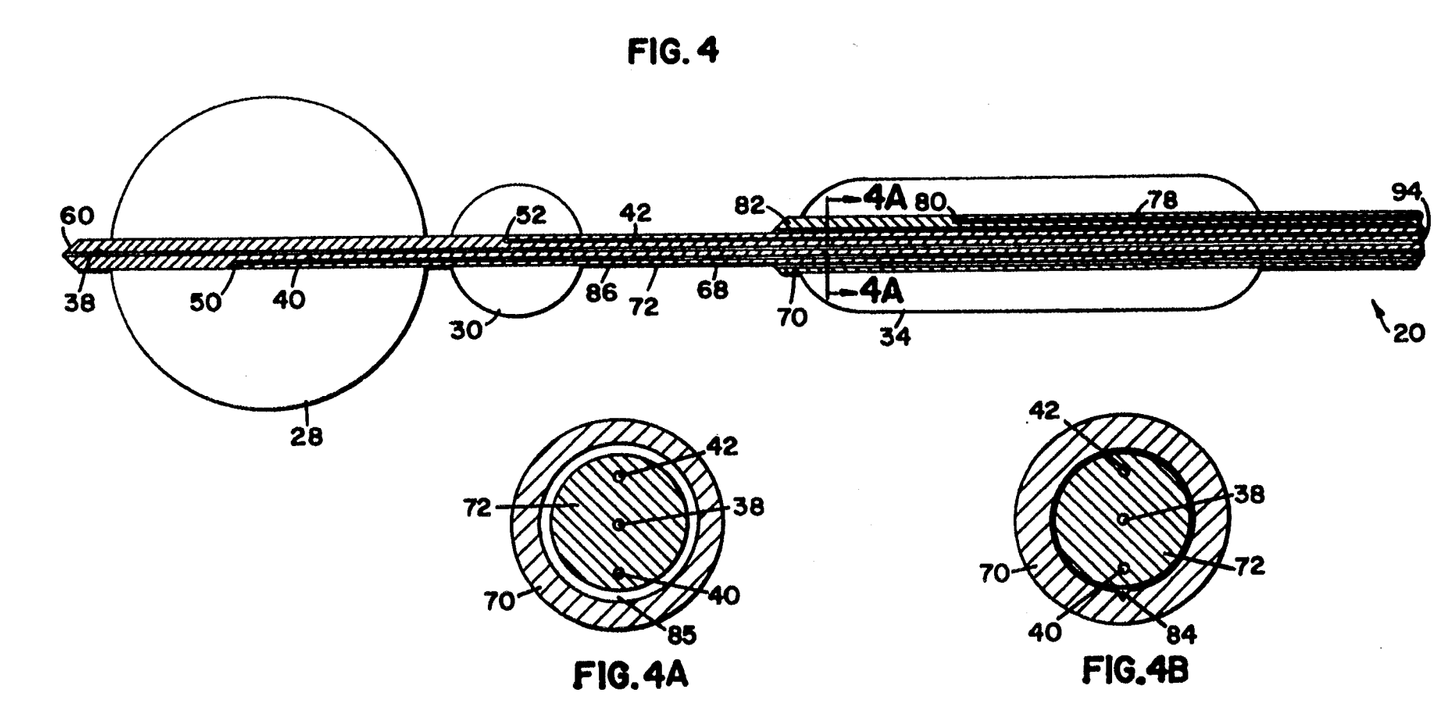
FIG. 4 is a cross-sectional view of one alternative embodiment of a catheter according to the present invention in which the catheter body is telescoping.
FIG. 4A is a cross-sectional view along the longitudinal axis of the catheter of FIG. 4, taken along Line 4A—4A.
FIG. 4B is a cross-sectional view along the longitudinal axis of another alternative embodiment of a telescoping catheter according to the present invention.

Referring now to FIG. 4, a further alternative embodiment comprises a telescoping catheter body 68 comprised of a tubular portion or part 70 and an extendable portion or part 72, which is inserted within and extends the entire length of tubular portion 70. Thus, extendible portion 72 slidably engages tubular portion 70. Tubular portion 70 includes an inner surface 82 within which tubular portion 72 slides.

In this embodiment, positioning balloon 28 and distal occlusion balloon 30 are attached to extendable portion 72 in a manner identical to that described above. Proximal occlusion balloon 34 is attached to tubular portion 70.

Extendable portion 72 defines a drainage lumen 38, first inflation lumen 40, first inflation port 50, second inflation lumen 42, and second inflation port 52. First inflation lumen 40 extends from a position proximate proximal end 94 of extendable portion 72 to a position proximate positioning balloon 28. First inflation port 50 passes from first inflation lumen 40 to the interior of positioning balloon 28. Second inflation lumen 42 extends from a position proximate the proximal end 94 of catheter body 68 to a position proximate distal occlusion balloon 30. Second inflation port 52 passes from second inflation lumen 42 to the interior of distal occlusion balloon 30.

In the preferred embodiment, depicted in FIG. 4A in a cross-sectional view taken along the longitudinal axis, there is a slight gap 85 between the extendable portion 72 and the tubular portion 70. During delivery and transport, the fluid passes through the gap 85 to the prostatic urethra. Tubular portion 70 defines a third inflation lumen 78 that extends from the proximal end 94 to a position proximate proximal occlusion balloon 34. Third inflation port 80 extends from a third inflation lumen 78 to the interior of proximal occlusion balloon 34.

An alternative embodiment of the telescoping catheter is shown in cross-section in FIG. 4B. In this embodiment, a groove 84 extends along inner surface 82 of tubular portion 70. When extendable portion 72 is inserted within tubular portion 70, groove 84 and outside surface 86 of extendable portion 72 form a delivery lumen. Delivery lumen 88 extends along the length of tubular portion 70 so that end 96 of groove 84 opens at the end of tubular portion 70. Thus, delivery lumen 88 is in fluid communication with the gap between distal occlusion balloon 30 and proximal occlusion balloon 34.

One skilled in the art will realize that gap 85 and groove 84 could be replaced with a delivery lumen located in extendable portion 72. One skilled in the art will further realize that the delivery lumen could be alternatively placed in the tubular portion 70.

Use of this telescoping catheter is similar to the use of the embodiment described above. The major difference is that the telescoping catheter allows the medical personnel to adjust the distance between the occlusion balloons 30 and 34 so that the distance between the occlusion balloons 30 and 34 matches the length of the particular patient's prostatic urethra 90.

Before using the telescoping catheter, medical personnel will assess the length of the prostatic urethra 90 by measuring the size of the prostate gland. The size of the gland can be measured through currently available methods including a digital rectal exam, transrectal ultrasound, CT scan, or MRI. Before inserting the catheter, the medical personnel should adjust the distance between the occlusion balloons to match the length of the prostatic urethra 90. Simple gradations on the exposed portion of the extendable portion 72 of the catheter body would allow the user to know the exact distance between the occlusion balloons 30 and 34.

Further alternative embodiments utilize iontophoresis, electroporation, and phonophoresis to assist the transportation of the fluid into the prostatic ducts. These non-pressure means of transportation also enhance drug penetration across the prostatic epithelium and into prostatic tissue. These methods may also increase cellular penetration of certain agents. Examples of these agents include DNA, RNA, etc. These non-pressure means of transportation may also make penetration into prostatic calculi possible.

Figure 5:
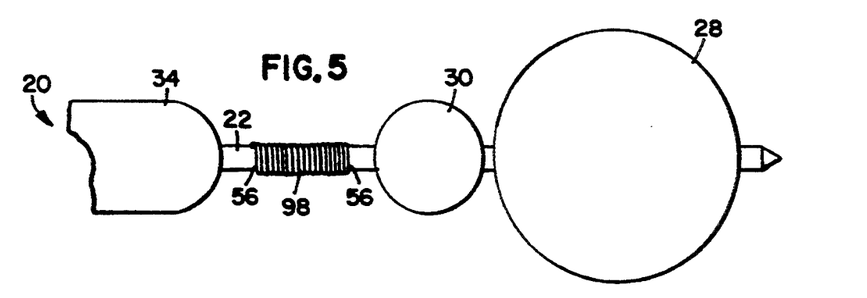
FIG. 5 is a partial view of an alternative embodiment of a catheter according to the present invention that includes a coil-wired electrode.
Figure 6:
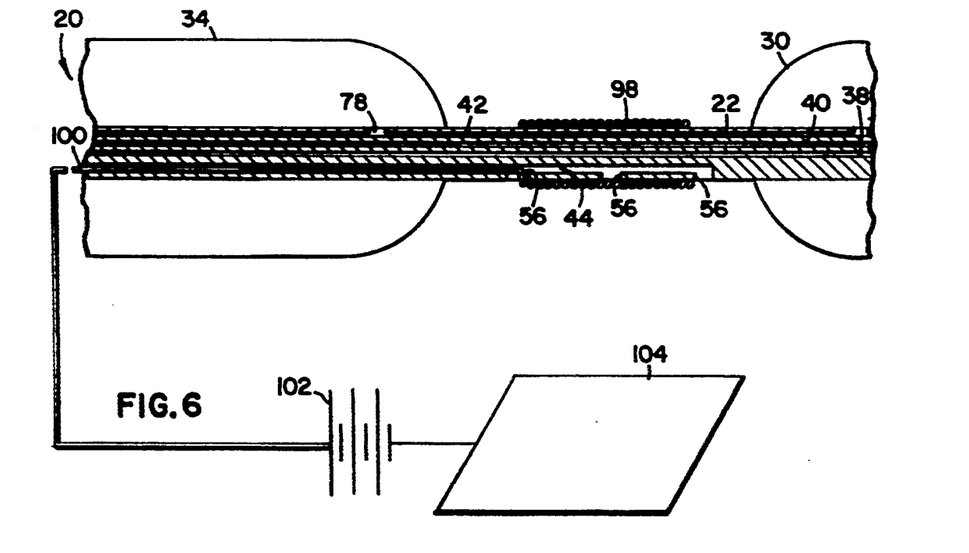
FIG. 6 is a partial cross-section of the catheter of FIG. 5 and further shows the coil-wired electrode connected to a power source and a patch-type electrode.

Referring now to FIGS. 5 and 6, a catheter that utilizes iontophoresis has a coil-wired electrode 98 that circumscribes catheter body 22 in the gap that is formed between distal occlusion balloon 30 and proximal occlusion balloon 34. Referring to FIG. 6, lead 100 passes through delivery lumen 44 and has one end attached to coil-wire electrode 100 and an opposite end attached to power supply 102. Patch-type return electrode 104 is also attached to power supply 102 and is mountable on a person's body. Alternatively, the return electrode can be mounted internally or on the catheter body 22 remote from electrode 98.

In operation, catheter 20 is located in the drug delivery position as described above. Coil-wire electrode 98 will be located within the prostatic urethra 90 when catheter 20 is in the drug-delivery position. Patch-type electrode 104 is then mounted on the patient's skin so that the prostate gland 92 is located between electrodes 98 and 104. Using the methods described above, drugs or diagnostic fluids are delivered to the prostatic urethra 90 and then pressurized so that they can be transported into the prostatic ducts. The electrodes 98 and 104 are then activated, which assists the transport. U.S. patent application Ser. Nos. 07/705,731 filed on May 24, 1991; 07/937,464 filed on Aug. 28, 1992; and 07/957,209 filed on Oct. 6, 1992 describe the use of iontophoresis in conjunction with catheters in greater detail and are incorporated by reference.

Figure 7:
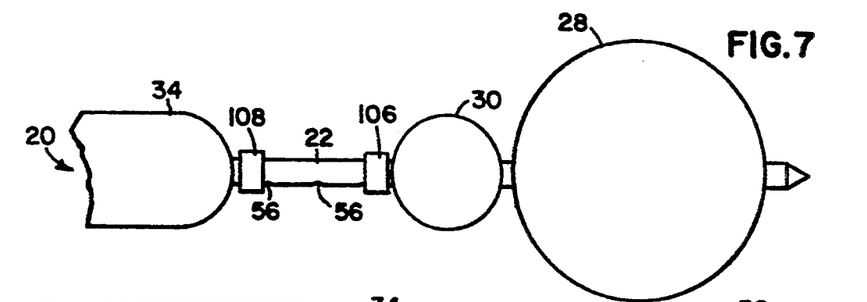
FIG. 7 is a partial view of an alternative embodiment of a catheter according to the present invention including first and second ring-type electrodes.
Figure 8:
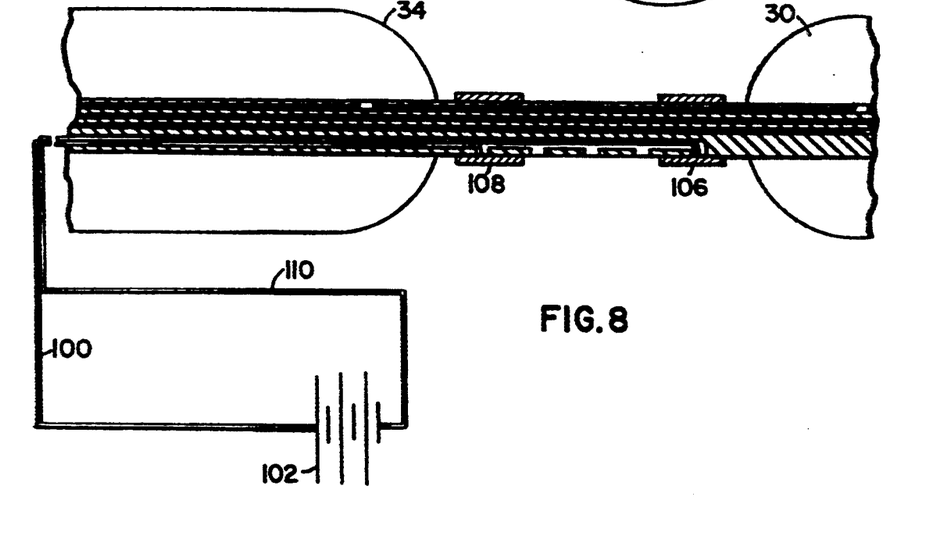
FIG. 8 is a partial cross-sectional view of the catheter of FIG. 7 and further shows the first and second ring-type electrode connected to a power source.

Referring to FIGS. 7 and 8, a catheter 20 which can be used for iontophoresis or electropolation has first and second ring-type electrodes 106 and 108 which circumscribe catheter body 22. First electrode 106 is proximate distal occlusion balloon 30 and second electrode 108 is proximate proximal occlusion balloon 34. Referring to FIG. 8, one end of leads 100 and 110 are connected to electrodes 106 and 108, respectively and are fed through delivery lumen 44. The opposite ends of leads 100 and 110 are connected to power supply 102. A catheter 20 that includes electrodes 98 and 104 for electroporation is used in a similar fashion to a catheter 20 that includes electrodes 106 and 108 for iontophoresis.

The primary difference is that the there is not a patch-type electrode 104 that must be placed against the patient's skin. U.S. patent application Ser. No. 08/129,252 filed on Sep. 29, 1993 describes the use of electroporation in conjunction with catheters in more detail and is incorporated by reference.

Figure 9:
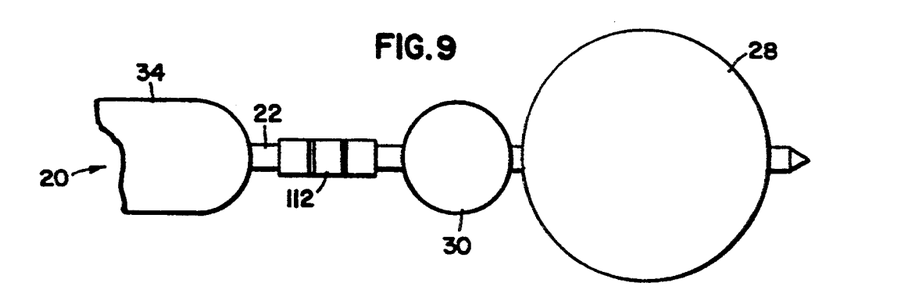
FIG. 9 shows an alternative embodiment of a catheter according to the present invention further comprising a transducer.
Figure 10:
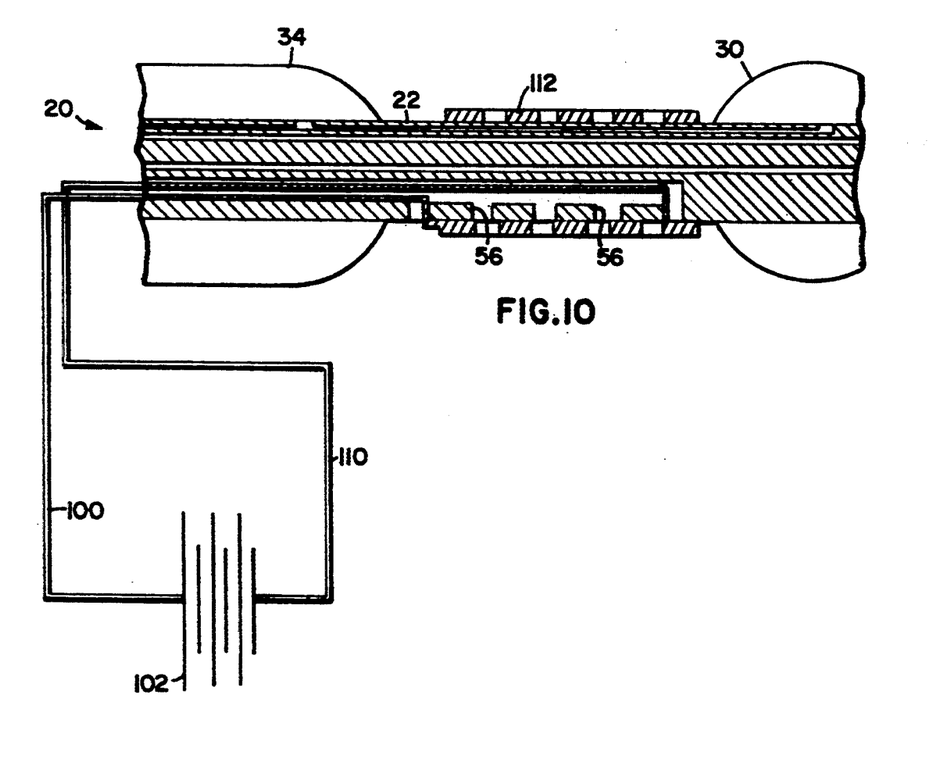
FIG. 10 is a partial cross-sectional view of the catheter of FIG. 9 and further shows the transducer connected to a power source.

Referring to FIGS. 9 and 10, a catheter 20 that utilizes phonophoresis has a tubular ultrasonic transducer 112 that circumscribes catheter body 22 in the gap between distal occlusion balloon 30 and proximal occlusion balloon 34. Referring to FIG. 10, leads 100 and 110 pass through delivery lumen 44 and have one end attached to ultrasonic transducer 112 and an opposite end attached to power supply 102. There is a slight gap between ultrasonic transducer 112 and catheter body 22 so that fluid can pass from delivery ports 56 into the prostatic urethra 90. A catheter 20 of the present invention that utilizes phonophoresis is used in a fashion similar to that described above for electroporation. U.S. patent application Ser. No. 07/937,464 on Aug. 28, 1992 describes the use of phonophoresis in conjunction with catheters in more detail and is incorporated by reference.

Figure 11:
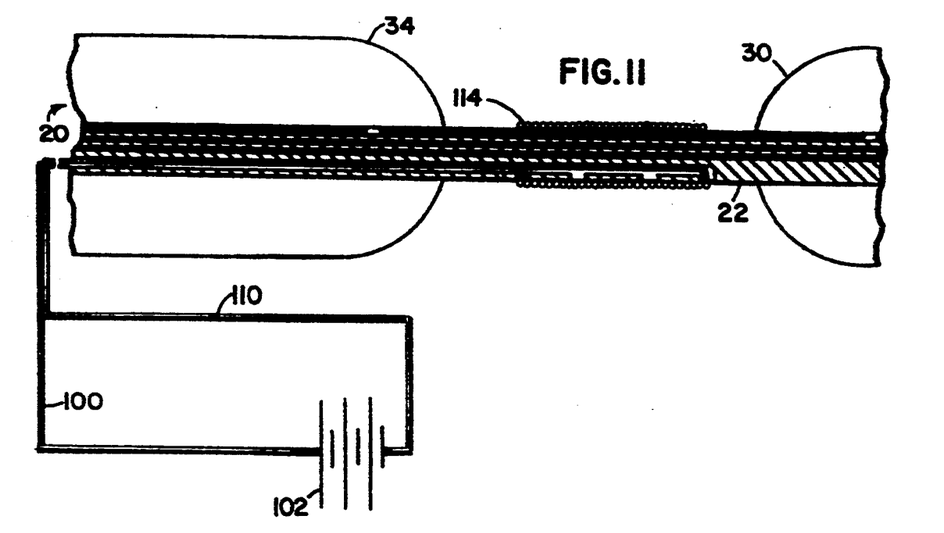
FIG. 11 is a partial cross-sectional view of an alternative embodiment of a catheter according to the present invention comprising a coil-type resistor connected to a power source.

Heating the prostatic tissue and the fluid as it is transported into the prostatic ducts and/or the prostatic tissue may also enhance efficiency of certain types of drugs, including oncolytics. Efficiency is improved by increasing tissue penetration and cellular uptake of the drug. Referring to FIG. 11, a catheter 20 of the present invention that employs heating has a coil-wire resistor 114 that forms a heating element. Coil-wire resistor 114 circumscribes catheter body 22 and is located between distal occlusion balloon 30 and proximal occlusion balloon 34.

Leads 100 and 110 pass through delivery lumen 44 and have a first end that is attached to coil-wire resistor 114 and a second end that is attached to power supply 102. A prostatic catheter 20 that utilizes heating is used in a fashion similar to that described above for electroporation or phonophoresis. One skilled in the art will realize that an ultrasonic transducer can be used in place of a coil-wire resistor to provide thermal energy within the prostatic urethra.

While the invention has been described in conjunction with a specific embodiment thereof, it is evident that different alternatives, modifications, and variations will be apparent to those skilled in the art in view of the foregoing description. Accordingly, the invention is not limited to these embodiments or the use of elements having specific configurations and shapes as presented herein.

The invention that we claim is:

1. A method of delivering fluid to a prostate gland of a patient, the method comprising the steps of:
   a) positioning a portion of a catheter within the prostatic urethra; the portion of the catheter within the prostatic urethra having a diameter less than the diameter of the prostatic urethra;
   b) isolating the prostatic urethra from the membranous urethra and the urinary bladder;
   c) delivering fluid through the catheter to the prostatic urethra, wherein most of the fluid is retained within the prostatic urethra; and
   d) pressurizing the fluid in the prostatic urethra to transport the fluid into the prostate gland.

2. The method of claim 1 wherein the catheter has a proximal end, a distal end, and a positioning balloon operably connected to the distal end, further wherein the step of positioning the catheter comprises the steps of:
- a) inserting the distal end of the catheter through the membranous urethra and through the prostatic urethra until the positioning balloon is located with the urinary bladder;
- b) inflating the positioning balloon; and
- c) applying retrograde tension to the catheter so that the positioning balloon becomes seated against the junction between the urinary bladder and the neck of the urinary bladder.

3. The method of claim 1 wherein the catheter further comprises first and second occlusion balloons, and further wherein the step of isolating comprises the steps of inflating the first and second occlusion balloons.

4. The method of claim 3 further comprising the step of adjusting the distance between the first and second occlusion balloons.

5. A method of delivering fluid to a prostate gland of a patient, the method comprising the steps of:
- a) positioning a portion of a catheter within the prostatic urethra; the portion of the catheter within the prostatic urethra having a diameter less than the diameter of the prostatic urethra;
- b) isolating the prostatic urethra from the membranous urethra and the urinary bladder;
- c) delivering fluid through the catheter to the membranous urethra, wherein most of the fluid is retained within the prostatic urethra; and
- d) transporting the fluid in the prostatic urethra into the prostate gland.

6. The method of claim 5 wherein the step of transporting includes pressurizing the fluid within the prostatic urethra.

7. The method of claim 5 wherein the step of transporting includes providing a voltage gradient across the prostate gland.

8. The method of claim 5 wherein the step of transporting includes heating the prostatic tissue.

9. The method of claim 5 wherein the step of transporting includes providing ultrasonic energy within the prostatic urethra.

* * * * *

REEXAMINATION CERTIFICATE (3271th)

United States Patent [19]
Hildebrand

[11] B1 5,419,763
[45] Certificate Issued Jul. 15, 1997

[54] PROSTATIC DRUG-DELIVERY CATHETER

[75] Inventor: Keith R. Hildebrand, Houlton, Wis.

[73] Assignee: CorTrak Medical, Inc., Roseville, Minn.

Reexamination Request:
No. 90/003,994, Oct. 6, 1995

Reexamination Certificate for:
| | |
|---|---|
| Patent No.: | 5,419,763 |
| Issued: | May 30, 1995 |
| Appl. No.: | 177,332 |
| Filed: | Jan. 4, 1994 |

[51] Int. Cl.⁶ ............................................. A61M 31/00
[52] U.S. Cl. ............................................. 604/54; 604/101
[58] Field of Search .................... 604/20, 21, 53, 604/54, 55, 96, 97, 98, 99, 100, 101, 19, 27, 28, 43, 48, 49; 606/192, 194

[56] References Cited

U.S. PATENT DOCUMENTS

| | | |
|---|---|---|
| 550,238 | 11/1895 | Allen, Jr. . |
| 3,977,408 | 8/1976 | MacKew . |
| 5,002,558 | 3/1991 | Klein et al. ............................. 606/192 |
| 5,342,306 | 8/1994 | Michael ................................. 604/101 |

FOREIGN PATENT DOCUMENTS

| | | |
|---|---|---|
| 0 438 078 A2 | 7/1991 | European Pat. Off. . |
| 0 474 906 A1 | 3/1992 | European Pat. Off. . |
| WO87/07510 | 12/1987 | WIPO . |
| WO88/03389 | 5/1988 | WIPO . |
| WO94/05361 | 3/1994 | WIPO . |

*Primary Examiner*—Michael Buiz

[57] ABSTRACT

A method and apparatus for the treatment of a prostate gland which isolates the prostatic urethra from the membranous urethra and the bladder so that fluid may be transported into the prostatic ducts without compromising the openings to the prostatic ducts. One preferred embodiment incorporates balloons located at either end of the prostatic urethra to isolate the same.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 5–9 are cancelled.

Claim 1 is determined to be patentable as amended.

Claims 2–4, dependent on an amended claim, are determined to be patentable.

New claims 10–16 are added and determined to be patentable.

1. A method of delivering fluid to a prostate gland of a patient, the method comprising the steps of:
   a) positioning a portion of a catheter within the prostatic urethra; the portion of the catheter within the prostatic urethra having a diameter less than the diameter of the prostatic urethra;
   b) isolating the prostatic urethra from the membranous urethra and the urinary bladder;
   c) delivering fluid through the catheter to the prostatic urethra *after the prostatic urethra is isolated*, wherein most of the fluid is retained within the prostatic urethra; and
   d) pressurizing the fluid in the prostatic urethra to transport the fluid into the prostate gland.

*10. A method of delivering fluid to a prostate gland of a patient, the method comprising the steps of:*
   *a) positioning a portion of a catheter within the prostatic urethra; the portion of the catheter within the prostatic urethra having a diameter less than the prostatic urethra;*
   *b) isolating the prostatic urethra from the membranous urethra and the urinary bladder;*
   *c) delivering fluid through the catheter to the prostatic urethra, wherein most of the fluid is retained within the prostatic urethra; and*
   *d) providing a voltage gradient across the prostate gland thereby transporting the fluid in the prostatic urethra into the prostate gland.*

*11. A method of delivering fluid to a prostate gland of a patient, the method comprising the steps of:*
   *a) positioning a portion of a catheter within the prostatic urethra; the portion of the catheter within the prostatic urethra having a diameter less than the prostatic urethra;*
   *b) isolating the prostatic urethra from the membranous urethra and the urinary bladder;*
   *c) delivering fluid through the catheter to the prostatic urethra, wherein most of the fluid is retained within the prostatic urethra; and*
   *d) providing ultrasonic energy within the prostatic urethra thereby transporting the fluid in the prostatic urethra into the prostate gland.*

*12. A method of delivering fluid to a prostate gland of a patient, the method comprising the steps of:*
   *a) positioning a portion of a catheter within the prostatic urethra, the portion of the catheter within the prostatic urethra having a diameter less than the prostatic urethra;*
   *b) isolating the prostatic urethra from the membranous urethra and the urinary bladder;*
   *c) delivering fluid through the catheter to the prostatic urethra, wherein most of the fluid is retained within the prostatic urethra; and*
   *d) pressurizing the fluid and iontophoretically transporting the fluid in the prostatic urethra into the prostate gland.*

*13. A method of delivering fluid to a prostate gland of a patient, the method comprising the steps of:*
   *a) positioning a portion of a catheter within the prostatic urethra; the portion of the catheter within the prostatic urethra having a diameter less than the diameter of the prostatic urethra;*
   *b) isolating the prostatic urethra from membranous urethra and the urinary bladder;*
   *c) delivering fluid through the catheter to the prostatic urethra, wherein most of the fluid is retained within the prostatic urethra; and*
   *d) pressurizing the fluid in the prostatic urethra to transport the fluid into tissue substantially throughout the prostate gland.*

*14. A method of delivering fluid to a prostate gland of a patient, the method comprising the steps of:*
   *a) positioning a portion of a catheter within the prostatic urethra; the portion of the catheter within the prostatic urethra having a diameter less than the diameter of the prostatic urethra;*
   *b) isolating the prostatic urethra from the membranous urethra and the urinary bladder;*
   *c) delivering fluid through the catheter to the prostatic urethra, wherein most of the fluid is retained within the prostatic urethra; and*
   *d) pressurizing the fluid in the prostatic urethra to transport the fluid into tissue deep within the prostate gland.*

*15. A method of delivering fluid to a prostate gland of a patient, the method comprising the steps of:*
   *a) positioning a portion of a catheter within the prostatic urethra; the portion of the catheter within the prostatic urethra having a diameter less than the diameter of the prostatic urethra;*
   *b) isolating the prostatic urethra from the membranous urethra and the urinary bladder;*
   *c) delivering fluid through the catheter to the prostatic urethra, wherein most of the fluid is retained within the prostatic urethra; and*
   *d) pressurizing the fluid in the prostatic urethra to transport the fluid into ducts, ductile, and acini within the prostate gland.*

*16. A method of delivering fluid to a prostate gland of a patient, the method comprising the steps of:*
   *a) positioning a portion of a catheter within the prostate urethra, the portion of the catheter within the prostatic urethra having a diameter less than the prostatic urethra;* b) isolating the prostatic urethra from the membranous urethra and the urinary bladder;

c) delivering fluid through the catheter to the prostatic urethra, wherein most of the fluid is retained within the prostatic urethra; and d) pressurizing the fluid and phonophoretically transporting the fluid in the prostatic urethra into the prostate gland.

* * * * *